United States Patent
Yu (10) Patent No.: US 9,796,988 B2
(45) Date of Patent: Oct. 24, 2017

(54) PROCESSES FOR PRODUCING MICROBIAL COPOLYESTERS FROM SUCROSE-CONTAINING FEEDSTOCKS

(75) Inventor: Jian Yu, Honolulu, HI (US)

(73) Assignee: BIO-ON S.p.A., San Giorgio di Piano (BO) (IT)

(*) Notice: Subject to any disclaimer, the term of this patent is extended or adjusted under 35 U.S.C. 154(b) by 372 days.

(21) Appl. No.: 14/358,911

(22) PCT Filed: Nov. 17, 2011

(86) PCT No.: PCT/IB2011/055164
§ 371 (c)(1),
(2), (4) Date: Sep. 9, 2014

(87) PCT Pub. No.: WO2013/072723
PCT Pub. Date: May 23, 2013

(65) Prior Publication Data
US 2014/0377819 A1  Dec. 25, 2014

(51) Int. Cl.
*C12P 7/62*  (2006.01)

(52) U.S. Cl.
CPC .................. *C12P 7/625* (2013.01)

(58) Field of Classification Search
CPC ...................................... C12P 7/625
See application file for complete search history.

(56) References Cited

U.S. PATENT DOCUMENTS

| | | | | |
|---|---|---|---|---|
| 989,876 | A * | 4/1911 | Rosenow | B30B 9/12 100/131 |
| 4,066,502 | A * | 1/1978 | Asai | C12P 13/08 435/110 |
| 2010/0092422 | A1* | 4/2010 | Ushida | A61K 31/78 424/78.37 |
| 2011/0059204 | A1* | 3/2011 | Jackson | C12P 7/6427 426/33 |
| 2011/0070180 | A1* | 3/2011 | Ranade | A61K 8/11 424/70.121 |
| 2012/0133073 | A1* | 5/2012 | Pacorel | C08F 8/14 264/128 |

FOREIGN PATENT DOCUMENTS

| | | |
|---|---|---|
| JP | 05-032768 A | 2/1993 |
| JP | 06-009761 A | 1/1994 |
| JP | 06-022773 A | 2/1994 |
| WO | 2011/045625 A1 | 4/2011 |

OTHER PUBLICATIONS

Gonzalez et al. Biotechnol. Bioengineer. (1986) XXVIII: 288-293.*
Chang et al. Bioresource Technology (2007) 98: 1448-1453.*
First Office Action from Japanese Patent Office dated Jul. 30, 2015 (with English translation of the Examiner's comments).
Machine translation of JP05-032768A.
Machine translation of JP06-009761A.
Machine translation of JP06-022773A.
International Search Report in corresponding PCT application dated Aug. 14, 2012.
Yu et al., Microbial Utilization and Biopolyester Synthesis of Bagasse Hydrolysates; Bioresource Technology, vol. 99, 2008, pp. 8042-8048.
Yu, Biosynthesis of Polyhydroxy Alcanoates from 4-Ketovaleric Acid in Bacterial Cells; Cheng, Ed., Green Polymer Chemistry, 2010, American Chemical Society, Washington, D.C., pp. 161-173.
Silva et al., Poly-3-hydroxybutyrate (P3HB) Production by Bacteria from Xylose, Glucose and Sugarcane Bagasse Hydrolysate, Journal of Industrial Microbiology and Biotechnology, vol. 31, 2004, pp. 245-254.
Da Cruz Pradella, High Cell-Density Poly(3-Hydroxybutyrate) Production from Sucrose Using Burkholderia sacchari Culture in Airlift Bioreactor, Bioresource Technology, vol. 101, 2010, pp. 8355-8360.
Wang et al., Synthesis of PHAs from Waster Under Various C:N Ratios, Bioresource Technology, vol. 98, 2007, pp. 1690-1693.
Aremu et al., Production of Polyhydroxybutyrate (PHB) by Pseudomonas putida Strain KT2440 on Cassava Hydrolysate Medium, Research Journal of Chemical Sciences, vol. 1, Jul. 2011, pp. 67-73.

* cited by examiner

Primary Examiner — Susan Hanley
(74) Attorney, Agent, or Firm — MH2 Technology Law Group, LLP (57) ABSTRACT

A process for producing hydroxyalkanoate copolymers, which comprises: (i) pre-treating a sucrose-containing feedstock in an acidic solution; (ii) feeding the pre-treated feedstock into a bioreactor containing polyhydroxyalkanoate producing microbial cells; (iii) cultivating the polyhydroxyalkanoate producing microbial cells to form a cell mass containing the hydroxyalkanoate copolymers; (iv) recovering the hydroxyalkanoate copolymers from the cell mass. The pre-treating step has the main function of hydrolyzing sucrose into glucose and fructose, which in turn are converted into 4-ketovaleric acid to give a mixture of mono-saccharides and organic precursors for microbial synthesis of hydroxyalkanoate copolymers, and particularly of PHBVV ter-polymers. Complex and expensive purification processes of the substrates obtained from the pre-treating step are not needed. The solutions can be directly used as the feeding solutions for microbial PHA biosynthesis.

18 Claims, 5 Drawing Sheets

PROCESSES FOR PRODUCING MICROBIAL COPOLYESTERS FROM SUCROSE-CONTAINING FEEDSTOCKS

BACKGROUND OF THE INVENTION

The present invention relates to a process for producing microbial copolyesters, particularly microbial hydroxyalkanoate copolymers, from sucrose-containing feedstocks.

Polyhydroxyalkanoates (PHAs) are a family of biopolyesters synthesized and accumulated in bacterial cells as carbon and energy storage. The biopolyesters can be melted and molded like conventional plastics, but completely biodegraded in the environment. Since PHA bioplastics are produced from renewable feedstocks, their fossil energy consumption and greenhouse gas emissions are much lower than those of petroleum-based counterparts.

Poly-(3-hydroxybutyrate), usually identified as P3HB or PHB, is the most common PHA formed by microorganisms from carbohydrates, and can be represented by the following formula:

P3HB

Formation of other PHAs often needs precursors or structurally related substrates. The hydroxyalkanoate monomers generated via metabolism in native microbial species are usually 3-hydroxyalkanoates (3HAs) in R configuration due to the stereo-specificity of enzymes in PHA biosynthesis.

Because of high stereo-regularity, the biopolyesters exhibit some unique properties such as optical activity, biodegradability, biocompatibility, and high crystallinity of some PHA polymers. For instance, P3HB has a high crystallinity of up to 70%, resulting in a rigid material with high melting temperature (180° C.), high elastic modulus (3.5 GPa), high tensile strength (43 MPa), but low elongation at break (5%). It therefore has limited applications.

The ductility of P3HB can be improved by introducing large side groups, such as ethyl groups, onto the polyester backbone, to form a co-polyester, poly(3-hydroxybutyrate-co-3-hydroxyvalerate), usually identified as P3HB3HV or PHBV, having formula:

P3HB3HV

Compared to PHB, a PHBV co-polyester (HB:HV=90:10) has a lower crystallinity (60%), lower melting point (140° C.), lower elastic modulus (0.8 G Pa), lower tensile strength (20 M Pa), but higher elongation at break (50%) The 3HV monomers, however, can be incorporated into the crystal lattice of P3HB, a phenomenon called isodimorphism which reduces the function of ethyl group (see e.g. the article by P. J. Barham, P. Barker, S. J. Organ, *FEMS Microbiol. Lett.* 103: 289-298 (1992)).

By incorporating a long monomer, such as 4-hydroxybutyrate (4HB) into the PHA backbone, crystallinity can also be reduced, and hence properties of the material can be modified. For instance, a co-polyester, P3HB4HB (3HB: 4HB=84:16), having formula:

P3HB4HB has a crystallinity of 45%, tensile strength of 26 MPa, and elongation at break of 400% (see the article by Z. Zhu, P. Dakwa, P. Tapadia, R. W. Whitehouse, S. Q. Wang, *Macromolecules* 36: 4891-4897. (2003)). The long monomer seems quite efficient in improving the ductility of co-polyesters. A high content of 4HB, however, results in low tensile strength and slow crystallization.

A ter-polyester, poly(3-hydroxybutyrate-co-3-hydroxyvalerate-co-4-hydroxyvalerate) (3HB:3HV:4HV=0.8:69.2:30)—usually identified as P3HB3HV4HV or PHBVV—having formula:

P3HB3HV4HV was synthesized from 4-ketovaleric acid by using the bacterium *P. putida* GPp1O4. The ter-polyester is solidified very slowly from melt, which may pose a great challenge to thermal processing and fabrication of the bioplastic (see the article by V. Gorenflo, G. Schmack, R. Vogel and A. Steinbuchel, *Biomacromolecules*, 2: 45-57 (2001)).

In microbial PHA biosynthesis, the monomers of 3HV, 4HB and 4HV are often derived from precursors or structural related chemicals such as propionic acid, 1,4-butanediol and 4-ketovaleric acid, either as a sole carbon source or a co-substrate with common carbon sources such as glucose. The precursors, however, are often much more expensive than glucose or carbohydrates, thus remarkably contributing to high production costs of PHA bioplastics. *Raistonia eutropha* is a representative PHA-producer and can accumulate PHA polymers up to 70-80 wt % of cell mass. This non-sporulating, gram-negative aerobe grows on simple carbon sources and mineral salts. In the presence of glucose and propionic acid or valeric acid, *R. eutropha* synthesizes P3HB3HV co-polymers with a 3HV content of 5 to 25 mol %. Because of relatively inefficient incorporation of the organic acids into PHA backbone, a high acid concentration is often maintained in the culture medium, resulting in a high toxicity to the cells.

In U.S. Pat. No. 5,364,778 a possible solution to the above problem is disclosed, wherein a microbiological process for producing copolymers comprising HB and HV monomer units using a PHB accumulating bacterium which is not capable of significant growth when cultivated under non growth limiting conditions on a substrate consisting essentially of a HV component. Therefore, at least part of the cultivation is conducted under growth limitation conditions, i.e. under conditions wherein an essential requirement for growth but not copolymer accumulation would be limited. Under such growth limitation conditions the tendency of the bacterium to produce and accumulate PHB homopolymer would be avoided, and the production and accumulation of HV containing copolymer would be induced.

SUMMARY OF THE INVENTION

The Applicant has faced the problem of producing biodegradable polyesters having a combination of material strength and ductility so as to make them suitable for a broad range of applications. The Applicant has focused its efforts on hydroxyalkanoate copolymers, and particularly on PHBVV ter-polymers, whose production by microbial fermentation, as explained above, shows many drawbacks, mainly due to the high cost of organic precursors for 3HV and 4HV monomers, the inefficient incorporation of HV monomers into the polyester backbone, to the toxicity of organic precursors to the microbial cells and to the high production costs of the overall process.

It should be noted that, within the present description and claims, the term "copolymer" (or "copolyester") includes any polymer (or polyester) consisting of at least two different comonomers, particularly it includes both co-polymers, namely polymers formed by two different monomers (such as P3HB3HV and P3HB4HB) and ter-polymers, namely polymers formed by three different monomers (such as P3HB3HV4HV).

The Applicant has found that hydroxyalkanoate copolymers can be efficiently produced by microbial fermentation of sucrose feedstocks, which are pre-treated in acidic hydrolysis so as to transform sucrose into glucose and fructose, which in turn are converted into 4-ketovaleric acid to give a mixture of mono-saccharides and organic precursors for microbial synthesis of hydroxyalkanoate copolymers.

Therefore, according to a first aspect, the present invention relates to a process for producing hydroxyalkanoate copolymers, which comprises:
  (i) pre-treating a sucrose-containing feedstock in an acidic solution;
  (ii) feeding the pre-treated feedstock into a bioreactor containing polyhydroxyalkanoate producing microbial cells;
  (iii) cultivating the polyhydroxyalkanoate producing microbial cells to form a cell mass containing the hydroxyalkanoate copolymers;
  (iv) recovering the hydroxyalkanoate copolymers from the cell mass.

The pre-treating step in an acidic medium is preferably carried out by: (i-a) acidifying the sucrose-containing feedstock to achieve a pH value of from 1.0 to 4.0, preferably from 2.0 to 3.0; and (i-b) heating the acidified sucrose-containing feedstock at a temperature of from 70° C. to 250° C., preferably from 100° C. to 200° C.

The pre-treating step has the main function of hydrolyzing sucrose into glucose and fructose, which in turn are converted into 4-ketovaleric acid to give a mixture of monosaccharides and organic precursors for microbial synthesis of hydroxyalkanoate copolymers, and particularly of PHBVV ter-polymers. Because microbial cells perform like individual "mini-plants" in which only the substrate molecules are transported, metabolized and synthesized into PHA polymers, complex and expensive purification processes of the substrates obtained from the pre-treating step are not needed. The solutions can be directly used as the feeding solutions for microbial PHA biosynthesis. The biopolyesters accumulated in cells can be easily recovered from aqueous medium for further purification. The in-situ formation of the precursor from hexoses resulted to be highly effective for the subsequent steps of microbial biosynthesis, with much lower costs with respect to the addition of pure organic precursors such as valeric acid and 4-ketovaleric acid.

Before PHA fermentation, the feedstocks or medium should be sterilized to remove wild type species that would compete with PHA-producing cells for carbon source and nutrients, resulting in a low PHA yield and substantial amount of non-PHA biomass to be removed. According to the present invention, the pre-treatment step is also a sterilization operation that has beneficial effects for the subsequent microbial biosynthesis and consumes little extra energy in comparison with a conventional PHA fermentation. Furthermore, the pretreated sugar solution is directly used for hydroxyalkanoate copolymer production to save the cost of additional operations for purification of carbohydrates and organic precursors.

DETAILED DESCRIPTION OF THE INVENTION

With "sucrose-containing feedstock" it is meant any substrate that can be metabolized by PHA-producing microbial cells, which contains sucrose, possibly in mixture with other carbohydrates, and which can be obtained from processing of organic vegetable raw materials, such as fruit juice, sugar cane molasses, sugar beet pulp, sugar beet molasses, and the like. The feedstock, besides sucrose and possibly other carbohydrates, may contain additional organic growth factors, N, P and/or other minerals as nutrients for the cell growth.

The pre-treatment step is preferably carried out in an autoclave or in a reactor. The acidification of the feedstock is preferably obtained by adding an acid substance, preferably a Brønsted acid such as hydrochloric acid, sulfuric acid, phosphoric acid, or mixtures thereof, in an amount so as to obtain the desired pH value as indicated above. It should be taken into account that solids usually present in the sucrose-containing feedstock, which derive from the previous processing of the vegetable raw material, may have a strong buffering capacity, namely they are able to react or combine with H$^+$ ions so as to reduce the concentration of free protons and thus the overall acidity. Therefore, the amount of the acid substance to be added to the feedstock may be expressed as H$^+$/solid ratio, namely as the amount of H$^+$ ions (mmol) that shall be added to the feedstock to obtain the desired pH value per weight unit (g) of solids present in the feedstock. Usually, the above amount ranges from 0.1 to 3.0 mmol H$^+$/g, more preferably from 0.3 to 1.5 mmol H$^+$/g.

According to a preferred embodiment, the starting feedstock is previously diluted so as to obtain a solids concentration of from 5% to 30% by weight, more preferably from 10% to 20% by weight, since with higher solids concentrations (50% by weight or higher) formation of undesired by-products, such as humins or chars, may occur during the thermal hydrolysis step. Moreover, some other minor by-products may be generated from thermal hydrolysis of sucrose, glucose and fructose, such as formic acid, acetic acid, hydroxymethylfurfural (HMF), which may inhibit cell growth and PHA formation when their concentrations reach high levels: by controlling the reaction conditions according to the present invention, formation of those by-products can be substantially reduced so as to avoid undesired cell inhibition effects.

The pre-treatment step is preferably carried out for a time sufficient to obtain hydrolysis of sucrose into glucose and fructose, and subsequent conversion of the same into 4-ketovaleric acid to give a mixture of mono-saccharides and organic precursors. Preferably, the pre-treatment step is carried out for a time of from 15 min to 12 hours, more preferably from 30 min to 6 hours.

Before feeding it into the bioreactor, the pre-treated feedstock is preferably cooled down to ambient temperature (e.g. from 20° C. to 35° C.) and then directly introduced into the bioreactor (or fermentor). According to a preferred embodiment, the pre-treated feedstock is gradually added to feed the microbial cells according to an appropriate feeding strategy, which is important to control cell growth, polymer biosynthesis and copolymer composition. The latter is of great importance to determine the properties of the so obtained PHA copolymers. Taking into account that the cell behavior is not linear with time, the feeding rate of the pre-treated feedstock is preferably not constant over time. For instance, after a first addition of the pre-treated feedstock at the beginning of the fermentation, no further additions are made for a certain time (e.g. for about 8-15 hours), so as to allow cell growth and to keep concentrations of glucose and 4-ketovaleric acid within relatively low values (preferably, from 0 to 20 g/l for glucose and from 0 to 2 g/l for 4-ketovaleric acid). Afterwards, addition of the pre-treated feedstock can be restarted at a substantially constant rate.

In order to control copolymer composition, two different pre-treated feedstocks, prepared by pretreatment of sucrose-containing feedstocks as described above, may be preferably fed into the bioreactor, the first one containing glucose and fructose and substantially devoid of 4-ketovaleric acid, the second one containing glucose and 4-ketovaleric acid and substantially devoid of fructose. The first pre-treated feedstock is initially fed so as to promote cell growth, while keeping a C/N ratio not higher than 10 (high nitrogen nutrient content) (4-ketovaleric acid and other by-products are more inhibitive to the cells than sugars, and may result in a low cell density). During this stage, a small amount of PHB (generally lower than 10% by weight of the cell mass) is formed. Afterwards, feeding of the second pre-treated feedstock is started so as to form copolyesters. Also during this second stage, it is preferable to continue feeding of the first pre-treated feedstock along with the second one, so as to control the copolymer monomer composition and therefore the material properties. As mentioned above, a too high content of 3HV and 4HV may result in some disadvantages such as reduced strength and crystallization rate.

The bioreactor contains polyhydroxyalkanoate producing microbial cells, such as cells of Ralstonia eutropha strain. The cultivation step can be carried out at pH and temperature conditions suitable for fermentation. Generally, the temperature is kept within a range of from 25° C. to 45° C., preferably from 30° C. to 35° C.; the pH value is preferably maintained at a value of from 6.0 to 7.5, more preferably from 6.5 to 7.0.

Taking into account that the pre-treated feedstock is an acidic solution, in order to arrange the pH value during the cultivation step, a basic substance is preferably fed to the bioreactor, such as an ammonia aqueous solution, which is gradually added so as to maintain the pH value within the desired range. The added ammonia also provides nitrogen nutrient for cell growth. Other alkaline solutions such as sodium hydroxide and/or potassium hydroxide may replace ammonium solution to control the ratio of carbon to nitrogen (C/N) in the culture medium.

The recovery of the hydroxyalkanoate copolymers from the cell mass may be carried out according to known techniques, as described, for instance, in U.S. Pat. No. 7,514,525 and International Patent Application WO 2011/045625.

The following examples are provided to further illustrate the invention, but without limiting its scope.

EXAMPLE 1

A concentrated sugar beet juice containing 69 wt % of total solids and 65 wt % of sucrose was acidified with a HCl solution (30 wt %) in an amount corresponding to 0.56 mmol H$^+$/g solids. The pre-acidified beet juice was further diluted with water to obtain a total solid concentration of 20 wt %.

Figure 1:
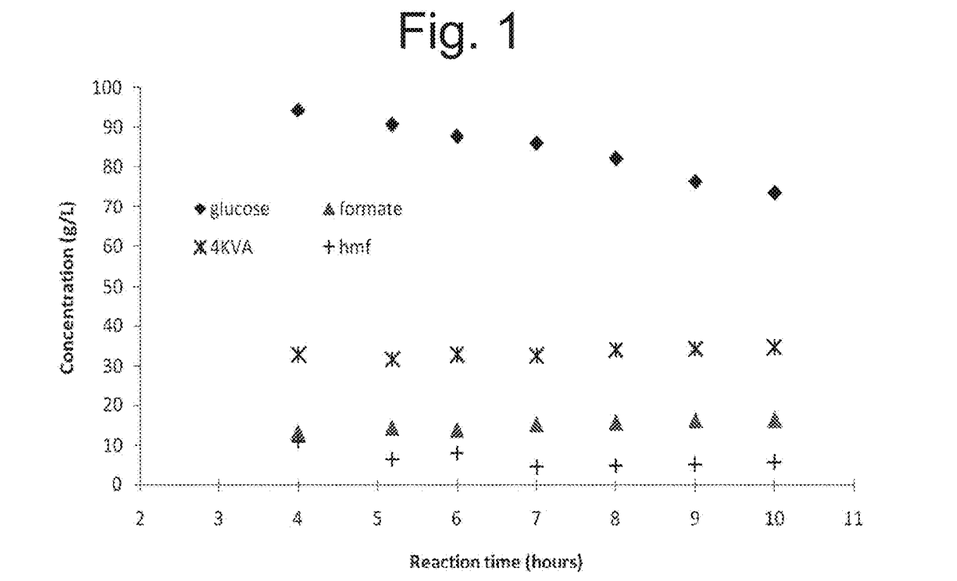
FIG. 1 is a graph that shows the concentrations of glucose, formic acid, 4-ketovaleric acid, and 5-hydroxymethylfurfural obtained over a period of 4 to 10 hours in an acidified sugar beet juice mixture.

The above acidified and diluted beet juice was treated at 170° C. and for a total time of 10 hours. Concentrations of glucose, formic acid, 4-ketovaleric acid (4-KVA) and 5-hydroxymethylfurfural (HMF) were monitored over time by analyzing samples of the treated juice (by means of HPLC). The results are reported in the graph of FIG. 1 as attached herewith. From those results, it appears that the concentration of 4-KVA was substantially stable after 4 hours of pre-treatment, while the concentration of HMF, a by-product which can be detrimental to cell growth and PHA formation, was reduced to less than 10 g/L by increasing the pre-treatment duration.

The so obtained hydrolysis solution was used for cultivation of a R. eutropha strain for PHA production. The solution contained 81 g/L of glucose, 36 g/L of 4-KVA, 16 g/L of formic acid, 4 g/L of HMF and 2 g/L of acetic acid. It was directly used as the feeding solution of the bioreactor without neutralization and detoxification. The culture was conducted in a bench top bioreactor under controlled conditions (30° C., dissolved oxygen>10% of air saturation and pH 6.4-6.8). The medium pH was controlled with an ammonia solution (15%) and the acidic hydrolysis solution. Starting with 1100 mL mineral solution for basic nutrients of cell growth, the hydrolysate solution was introduced into the bioreactor.

Figure 2:
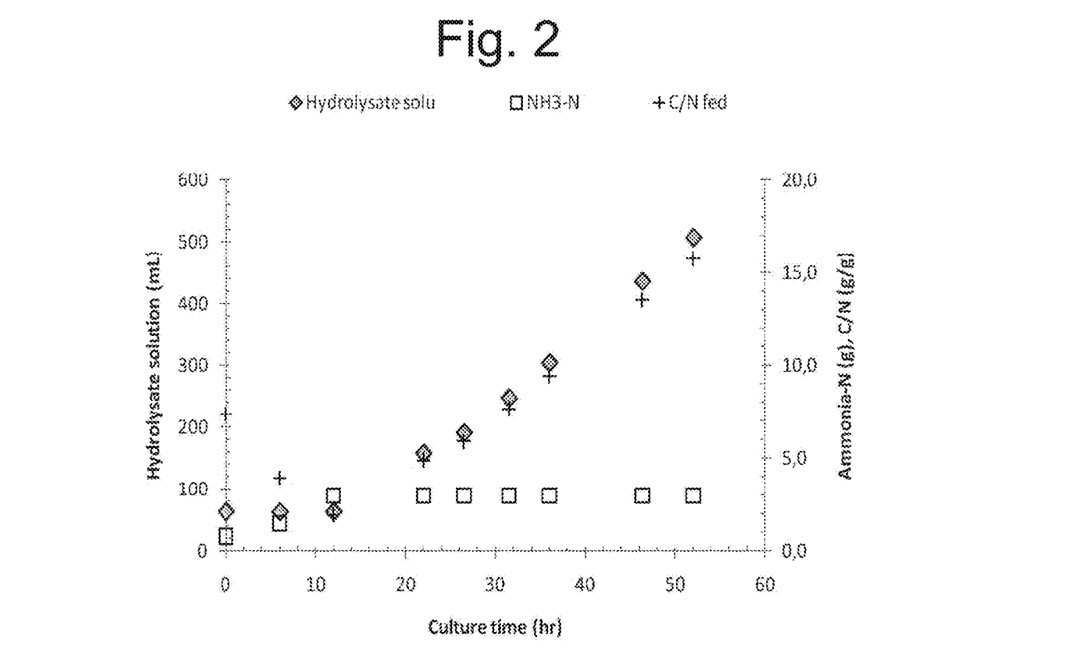
FIG. 2 is a graph that shows the accumulated volumes of the components obtained in FIG. 1 that are fed to the bioreactor.

The accumulated volumes of the various components fed to the bioreactor over time is reported in FIG. 2 as attached herewith.

Figure 3:
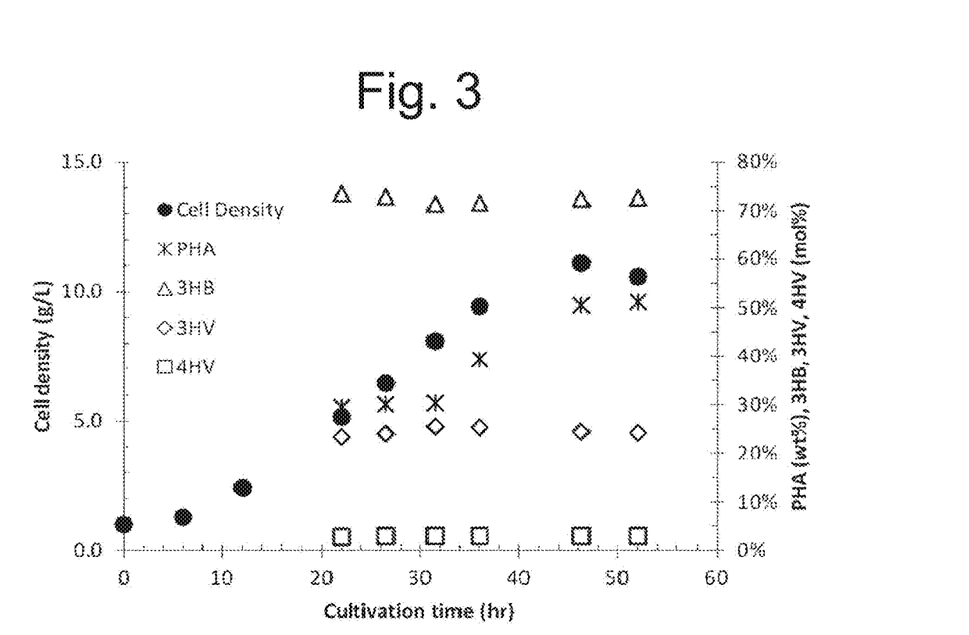
FIG. 3 is a graph that shows the cell density, PHA content and mole % of 3HB, 3HV and 4HV of the PHA obtained by the fermentation of the components of FIG. 2.

Corresponding to the feeding strategy of FIG. 2, the time courses of cell density, PHA content and mole % of 3HB, 3HV and 4HV of the PHA are reported in FIG. 3. The predominant monomer in PHBVV is 3HB (71-74 mol %), followed by 3HV (23-26 mol %), while 4HV is a minor component (2-3 mol %). By using one hydrolysis solution, the chemical composition of PHBVV can be controlled at a constant level in PHA fermentation.

Figure 4:
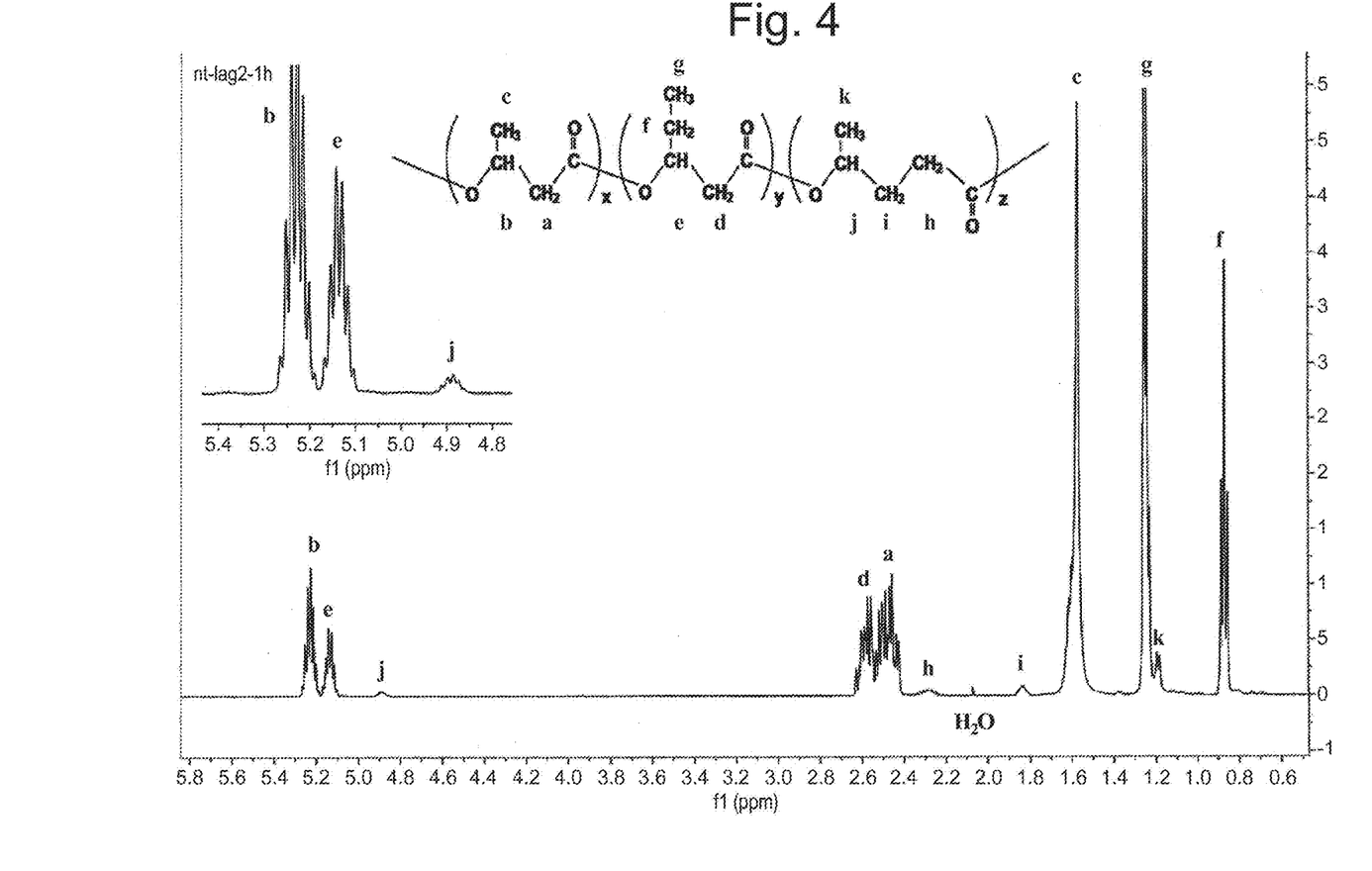
FIG. 4 is the 1H-NMR spectrum of the PHBVV obtained in the product depicted in FIG. 3.

In FIG. 4 the $^1$H-NMR spectrum of the so obtained PHBVV is reported.

EXAMPLE 2

A first hydrolysate solution (Solution A) was prepared via thermal hydrolysis of a sugar cane molasses solution (20 wt % sucrose, pH 2.6) at 120° C. for 40 min. The predominant hydrolysates were glucose and fructose with negligible amount of acetic acid, HMF and 4-ketovaleric acid. A second hydrolysate solution (Solution B) was obtained from a sugar beet solution with thermal hydrolysis at 170° C. for 5 hours (see Example 1, FIG. 1). The predominant hydrolysates were glucose (91 g/L) and 4-ketovaleric acid (32 g/L). The minor products included formic acid (14 g/L), HMF (6 g/L), acetic acid (1 g/L). No fructose was detected in Solution B.

Figure 5:
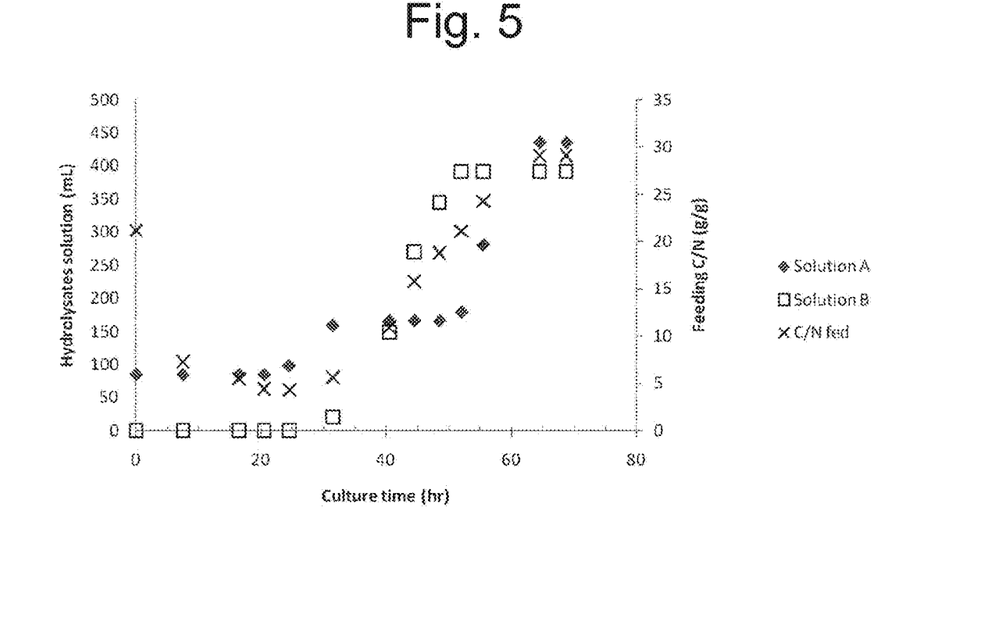
FIG. 5 shows the results obtained by feeding pre-treated feedstocks are fed into the bioreactor where the first feedstock contains glucose and fructose and is substantially devoid of 4-ketovaleric acid, and the second feedstock contains glucose and 4-ketovaleric acid and substantially devoid of fructose.

Starting with an initial mineral solution (1100 mL), the bioreactor was operated in fed-batch mode with a feeding strategy of Solutions A and B as represented in FIG. 5, wherein the accumulated volumes (mL) of Solutions A and B with time as well as the C/N ratio estimated from the original sucrose carbon and ammonia-N added.

Figure 6:
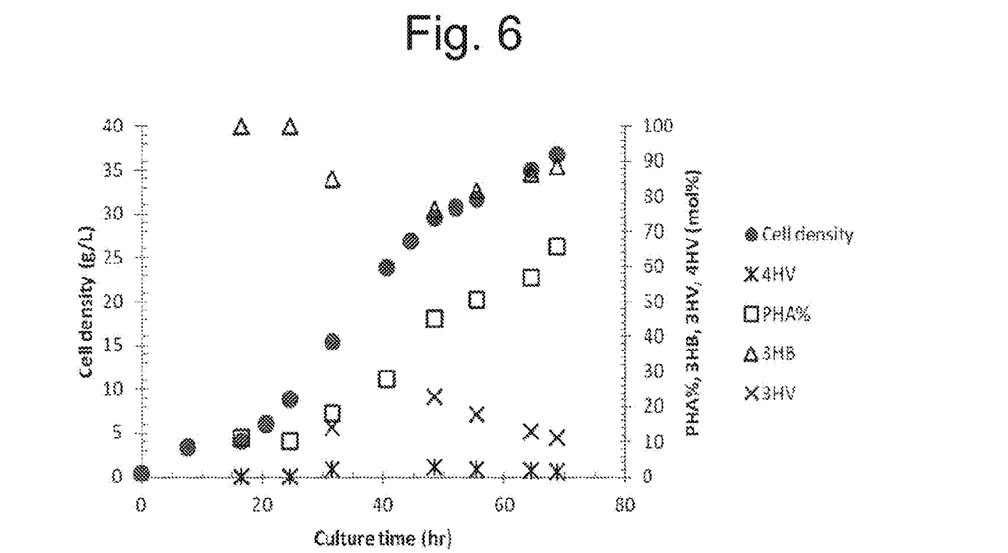
FIG. 6 is a graph that shows the cell density, PHA content and mole % of 3HB, 3HV and 4HV of the PHA obtained by the fermentation of the components of FIG. 5.

Corresponding to the feeding strategy of FIG. 5, the time courses of cell density, PHA content and mole % of 3HB, 3HV and 4HV of the PHA are reported in FIG. 6. Compared with Example 1 (FIG. 3), the overall content of 3HB was increased (88.4 mol %) while the contents of 3HV (11.0 mol %) and 4HV (0.6 mol %) were reduced. This is expected because Solution A substantially devoid of 4-ketovaleric acid was introduced at the beginning and the end of fed-batch culture. Indeed, when Solution A was used as sole carbon source, P3HB, a homo-polyester, was formed from glucose and fructose (data not shown here).

EXAMPLE 3

Pure P3HB and P3HB3HV4HV obtained according to Example 2 (3HB:3HV:4HV=88.4:11:0.6) were extracted from freeze-dried cell mass in hot chloroform. The dissolved polymers were precipitated out from chloroform by adding methanol gradually till white precipitates were formed (75% methanol and 25% chloroform). The polymers were filtered and dried in air and further in oven for later use.

Crystallization from Melt

Figure 7:
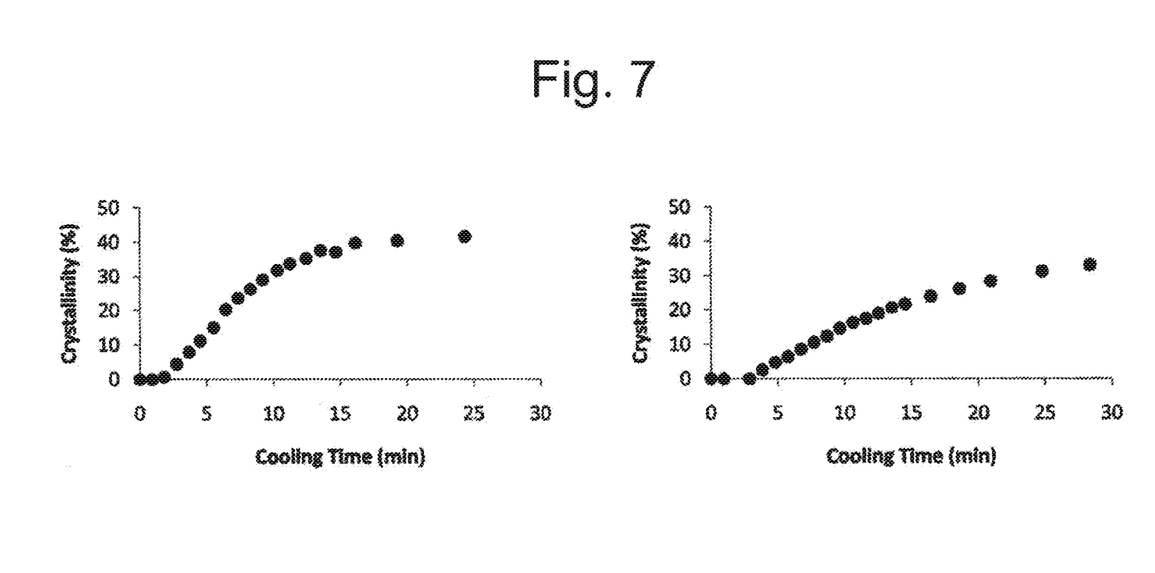
FIG. 7 comprises two graphs that plot the crystallinity of the biopolymers versus the cooling time.

The purified P3HB and P3HB3HV4HV were melted at 180° C. or 160° C. respectively, at ambient conditions for approximately 10 min and then placed immediately on the window of a Fourier Transform Infrared Spectroscopy (FTIR) equipped with attenuated total reflectance (ATR). When the melted polymers were cooled down, IR absorptions were continuously monitored to measure crystallization of the biopolyesters. The crystallinity of biopolymers were measured at wave number of 1184 cm$^{-1}$ and plotted against the cooling time. The results are reported in FIG. 7. P3HB had a higher crystallinity and faster crystallization rate than PHBVV.

The presence of 11 mol % of 3-HV and 0.6 mol % of 4-HV in PHA backbones not only reduces the crystallinity but also retards the crystallization process of PHBVV. Since a slow solidification of melted PHA may cause a problem in thermal processing of the bioplastics, controlling the chemical composition of PHBVV is therefore essential to make a bioplastics with desired thermal and mechanical properties.

Tensile Tests

Films of PHB and PHBVV were prepared by dissolving the purified PHA in hot chloroform. The solutions, after cooling to room temperature, were cast on clean glass surfaces into thin films (about 0.3 mm) The films were allowed to age in air for 5, 15 and 25 days. The films were cut into thin strips (10 mm) with approximate cross-sectional areas of 3-4 mm$^2$ and an initial length of 25 mm. The strips were placed in a tensile testing machine and loaded until failure to break. The mechanical properties are reported in Table 1:

TABLE 1

| Properties | PHB | | | PHBVV | | |
|---|---|---|---|---|---|---|
| Molecular weight (M$_v$) | 243,000 | | | 210,000 | | |
| Melting point (° C.) | 170-180 | | | 150-160 | | |
| Age (days) | 5 | 15 | 25 | 5 | 15 | 25 |
| Crystallinity (%) | 52.52 | 54.60 | 58.65 | 41.79 | 41.94 | 45.58 |
| Elastic modulus (GPa) | 0.86 | 1.14 | 1.16 | 0.32 | 0.37 | 0.43 |
| Tensile strength (MPa) | 23.20 | 28.36 | 29.78 | 10.80 | 11.73 | 13.09 |
| Elongation at break (%) | 16.6 | 6.5 | 4.9 | — | — | 105 |

The above tests clearly revealed that P3HB is a rigid material with high elastic modulus and low elongation at break, while P3HB3HV4HV has a relatively low elastic modulus but high elongation at break. The results also indicate that the films should be aged 25 days before tensile test to allow complete evaporation of solvent and crystallization of PHA molecules. Compared with the elongation at break (ductility) of PHB (5%) and PHBV (3HB:3HV=90:10) (50%) as reported in literature, PHBVV (3HB:3HV:4HV=88.4:11.0:0.6) obtained according to the present invention exhibits a higher ductility (105%) than PHBV, probably because of the presence of small amount of 4HV that disturb the crystalline of PHBV.

The invention claimed is:

1. A process for producing hydroxyalkanoate copolymers, the process comprising:
   (i) pre-treating a first sucrose-containing feedstock in a first acidic solution to obtain a first pre-treated feedstock containing glucose and fructose and substantially devoid of 4-ketovaleric acid;
   (ii) pre-treating a second sucrose-containing feedstock in a second acidic solution to obtain a second pre-treated feedstock containing glucose and 4-ketovaleric acid and substantially devoid of fructose;
   (iii) initially feeding the first pre-treated feedstock into a bioreactor containing polyhydroxyalkanoate-producing microbial cells;
   (iv) subsequently feeding the second pre-treated feedstock into the bioreactor containing the polyhydroxyalkanoate-producing microbial cells;

(v) cultivating the polyhydroxyalkanoate-producing microbial cells to form a cell mass containing the hydroxyalkanoate copolymers; and (vi) recovering the hydroxyalkanoate copolymers from the cell mass.

2. The process according to claim 1, wherein the pre-treating step (i) in the first acidic solution is carried out by: (i-a) acidifying the first sucrose-containing feedstock to achieve a pH value of from 1.0 to 4.0; and (i-b) heating the acidified first sucrose-containing feedstock at a temperature of from 70° C. to 250° C.

3. The process according to claim 1, wherein the first sucrose-containing feedstock is obtained from processing of organic vegetable raw materials selected from the group consisting of fruit juice, sugar cane molasses, sugar beet pulp, and sugar beet molasses.

4. The process according to claim 1, wherein in the pre-treating step the first sucrose-containing feedstock is acidified by adding an acid substance.

5. The process according to claim 4, wherein the acid substance is selected from: hydrochloric acid, sulfuric acid, phosphoric acid, and mixtures thereof.

6. The process according to claim 4, wherein the acid substance is added to the first sucrose-containing feedstock with a $H^+$/solid ratio of from 0.1 millimoles $H^+$/gram (mmol $H^+$/g) to 3.0 mmol $H^+$/g.

7. The process according to claim 1, wherein the first sucrose-containing feedstock is previously diluted so as to obtain a solids concentration of from 5% by weight to 30% by weight.

8. The process according to claim 1, wherein the pre-treating step (i) is carried out for a time of from 15 minutes to 12 hours.

9. The process according to claim 1, wherein the first pre-treated feedstock, before feeding into the bioreactor, is cooled down to ambient temperature and then directly introduced into the bioreactor.

10. The process according to claim 1, wherein the cultivation step is carried out at a temperature of from 25° C. to 45° C.

11. The process according to claim 1, wherein the cultivation step is carried out at a pH value of from 6.0 to 7.5.

12. The process according to claim 11, wherein to arrange the pH value during the cultivation step, a basic substance is fed to the bioreactor.

13. The process according to claim 4, wherein the acid substance is added to the first sucrose-containing feedstock with a $H^+$/solid ratio of from 0.3 millimoles $H^+$/gram (mmol $H^+$/g) to 1.5 mmol $H^+$/g.

14. The process according to claim 11, wherein to arrange the pH value during the cultivation step, an ammonia aqueous solution is fed to the bioreactor.

15. The process according to claim 1, wherein the pre-treating step (i) in the first acidic solution is carried out by: (i-a) acidifying the first sucrose-containing feedstock to achieve a pH value of from 2.0 to 3.0; and (i-b) heating the acidified first sucrose-containing feedstock at a temperature of from 100° C. to 200° C.

16. The process according to claim 1, wherein the first sucrose-containing feedstock is previously diluted so as to obtain a solids concentration of from 10% by weight to 20% by weight.

17. The process according to claim 1, wherein the pre-treating step (i) is carried out for a time of from 30 minutes to 6 hours.

18. The process according to claim 1, wherein the cultivation step is carried out at a temperature of from 30° C. to 35° C.

* * * * *